United States Patent [19]

Yamamoto et al.

[11] Patent Number: 5,424,455
[45] Date of Patent: Jun. 13, 1995

[54] HETEROCYCLIC COMPOUNDS FOR MAKING RED DISPERSE DYES

[75] Inventors: Jun Yamamoto, Osaka, Japan; Yasuyoshi Ueda, Munich, Germany; Junichi Sekihachi; Yosuke Yamamoto, both of Osaka, Japan; Takashi Omura, Hyogo, Japan

[73] Assignee: Sumitomo Chemical Co., Ltd., Osaka, Japan

[21] Appl. No.: 104,474

[22] Filed: Jul. 28, 1993

Related U.S. Application Data

[62] Division of Ser. No. 517,763, May 2, 1990, abandoned.

[30] Foreign Application Priority Data

May 11, 1989 [JP] Japan .................. 1-120058

[51] Int. Cl.$^6$ .................. C09B 57/00; D06P 3/54; C07D 493/04
[52] U.S. Cl. .................. 549/299; 8/636; 8/922; 540/524; 540/596; 544/148; 544/212; 544/378; 546/197; 546/270; 548/159; 548/204; 548/221; 548/236; 548/311.7; 548/463; 548/526; 549/57; 549/60
[58] Field of Search .................. 549/299, 57, 60; 540/524, 596; 544/148, 378; 546/197; 548/159, 204, 236, 526; 8/636, 922

[56] References Cited

U.S. PATENT DOCUMENTS

| | | | |
|---|---|---|---|
| 4,115,404 | 9/1978 | Greenhalgh et al. | 549/299 |
| 4,122,087 | 10/1978 | Greenhalgh et al. | 549/299 |
| 4,650,882 | 3/1987 | Kenyon et al. | 549/299 |
| 4,916,240 | 4/1990 | Kenyon | 549/299 |
| 5,077,416 | 9/1991 | Ueda et al. | 549/299 |
| 5,223,616 | 6/1993 | Yamamoto et al. | 549/299 X |

FOREIGN PATENT DOCUMENTS

| | | |
|---|---|---|
| 33583 | 8/1981 | European Pat. Off. . |
| 146269 | 6/1985 | European Pat. Off. . |
| 182507 | 5/1986 | European Pat. Off. . |
| 252406 | 1/1988 | European Pat. Off. . |
| 363034 | 4/1990 | European Pat. Off. .......... 549/299 |
| 2068402 | 8/1981 | United Kingdom . |
| 2103231 | 2/1983 | United Kingdom . |

OTHER PUBLICATIONS

Greenhalgh et al., "IV The Synthesis of Ouinodimethanes In The Benzodifuranone and Benodipyrrolidone Series" Dyes and Pigments, vol. 1 pp. 103–120 (1980).
Chemische Berichte, 30: 124 (1897).

Primary Examiner—Mary C. Lee
Assistant Examiner—Fiona Powers
Attorney, Agent, or Firm—Cushman Darby & Cushman

[57] ABSTRACT

A heterocyclic compound of the formula,

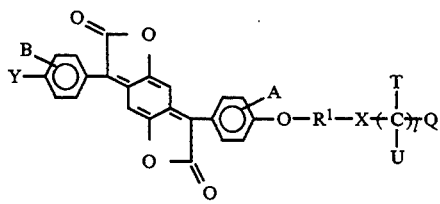

wherein A and B are each hydrogen, halogen, alkyl or alkoxy, $R^1$ is alkylene having upto 6 carbon atoms, X is direct linkage or divalent group such as —O—, —S— —and the like, T and U are each hydrogen or alkyl, l is 0 or 1 to 3, Q is 5-, 6- or 7- membered saturated or unsaturated heterocyclic residue, and Y is hydrogen, halogen, alkyl, alkoxy or

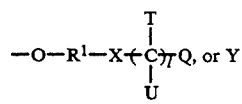

and B are taken together with each other to form methylene-dioxy, which is useful for dyeing or printing hydrophobic fiber materials with superior dyeability to give a dyed or printed product of a red color excellent in fastness properties, particularly those such as washing fastness.

14 Claims, No Drawings

HETEROCYCLIC COMPOUNDS FOR MAKING RED DISPERSE DYES

This is a division of application Ser. No. 07/517,763, filed May 2, 1990, now abandoned.

The present invention relates to heterocyclic compounds, their production and a process for dyeing or printing hydrophobic fiber materials therewith. More specifically, the present invention relates to benzodifuranone compounds useful for dyeing or printing hydrophobic fiber materials, for example, those such as polyester fibers and fiber materials containing the same, in a red color.

Disperse dyes useful for dyeing or printing hydrophobic fiber materials have been increasingly desired to have much superior dyeability and capability of giving dyed or printed products excellent in various fastness properties with consumers' trend toward higher grade clothings. Answering such trend to increase the added value of dyed or printed products of hydrophobic fibers or hydrophobic fiber containing fiber materials, they are often subjected to various after-finish treatments such as softening finish, antistatic finish, feel-improving finish and the like. However, these after-finish treatments usually carried out at relatively high temperatures encounter problems of dye bleed, so that the dyed or printed products deteriorate their wet fastness properties, particularly those such as washing fastness.

So far, many attempts to develop a red disperse dye capable of giving dyed or printed products excellent in washing fastness have been directed mainly toward azo compounds, so that many azo compounds have been proposed therefor. However, those known azo compounds are not yet sufficient to solve the problem such that the washing fastness of dyed or printed products becomes markedly poor after the finish treatments.

There are other attempts to develop benzodifuranone compounds useful for dyeing or printing hydrophobic fiber materials, as disclosed in, for example, JP-A-60-152567, 52-109526 and 56-122869. However, the benzodifuranone compounds are also insufficient to satisfy both dyeability and the fastness properties at the same time, and still awaiting for improvements.

It is the object of the present invention to provide disperse dye compounds having excellent dye properties for dyeing or printing hydrophobic fiber materials, particularly those such as polyester fiber materials, and capable of giving dyed or printed products excellent in fastness properties such as light fastness, sublimation fastness and wet fastness, particularly those such as washing fastness.

The present invention provides heterocyclic compounds of the following formula (I),

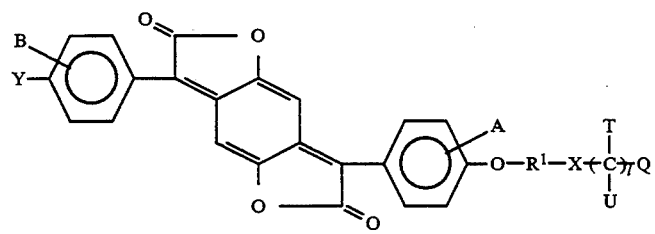

wherein A and B are each independently a hydrogen atom, a halogen atom, a $C_1$-$C_4$ alkyl group or a $C_1$-$C_4$ alkoxy group, $R^1$ is a methylene group or a straight or branched $C_2$-$C_6$ alkylene group unsubstituted or substituted by a hydroxy group, a $C_1$-$C_4$ alkoxy group or a $C_1$-$C_4$ alkylcarbonyloxy group, X is a direct linkage or a divalent group of

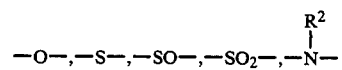

in which $R^2$ is a hydrogen atom or a $C_1$-$C_4$ alkyl group,

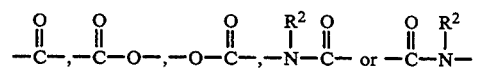

in which $R^2$ is as defined above, T and U are each independently a hydrogen atom or a $C_1$-$C_4$ alkyl group, l is 0 or an integer of 1 to 3, Q is an unsubstituted or substituted 5-, 6- or 7-membered saturated or unsaturated heterocyclic residue, and Y is a hydrogen atom, a halogen atom, a $C_1$-$C_4$ alkyl group, a $C_1$-$C_4$ alkoxy group or a group of the formula

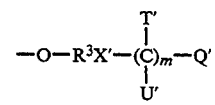

wherein $R^3$, X', T', U', m, and Q' are the same as or different from, respectively, $R^1$, X, T, U, l and Q, The present invention also provides a process for producing the heterocyclic compounds of the formula (I), which comprises reacting a mandelic acid of the following formula (II),

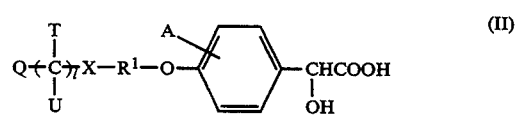

wherein A, $R^1$, X, T, U, l and Q are as defined above, with a compound of the following formula (III),

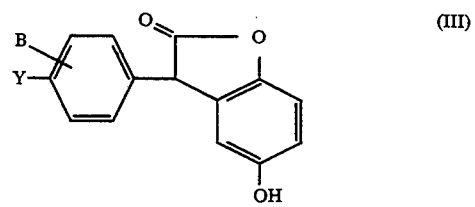

wherein B and Y are as defined above, followed by mild oxidation

The present invention further provides a process for dyeing or printing hydrophobic fiber materials, which comprises contacting the fiber materials with the heterocyclic compound of the formula (I).

In the above formula (I), the alkyl group represented by A or B includes, for example, methyl, ethyl, n-propyl, i-propyl and n-butyl, and the alkoxy group represented thereby includes, for example, methoxy, ethoxy, n-propoxy, n-butoxy and sec-butoxy.

In the present invention, A is preferably hydrogen, methyl or methoxy, and more preferably hydrogen, and B is preferably hydrogen and the alkoxy such as methoxy and butoxy, more preferably hydrogen.

The alkyl and alkoxy groups represented by Y include those exemplified above for the symbols A and B. In the present invention, Y is preferably hydrogen, methyl, alkoxy such as methoxy and butoxy, tetrahydrofurfuryloxy and 2-pyrrolidinoethoxy which are represented by the formula

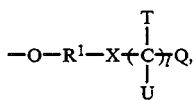

and methylenedioxy which can be formed taken together with B. Of these, particularly preferable Y is hydrogen.

When X is

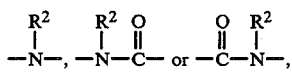

the alkyl group represented by R² includes methyl, ethyl and n-butyl. In the present invention, R² is preferably hydrogen and methyl.

With respect to the symbol X, preferable are

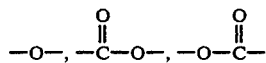

and direct linkage, and more preferably —O— and direct linkage.

The alkyl group represented by T or U includes those exemplified above for the symbols A and B. In the present invention, T and U are preferably each hydrogen.

When X is —O—, l is preferably an integer of 1 to 3, and more preferably 1 or 2, and when X is a direct linkage, l is preferably 0.

The unsaturated heterocyclic residue represented by Q includes furyl, thienyl, pyrrolyl, pyridyl, pyranyl, thiazolyl, oxazolyl, pyrazolyl, imidazolyl, thiadiazolyl and s-triazinyl, which are represented by the following formulas, respectively.

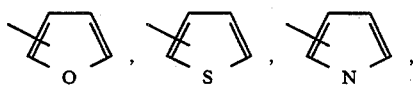

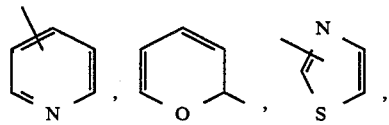

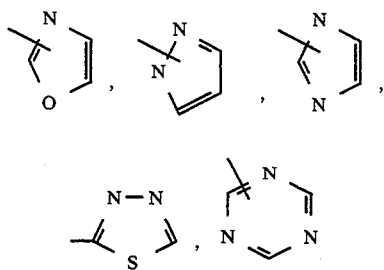

The saturated heterocyclic residue represented by Q includes those represented by the following formulas.

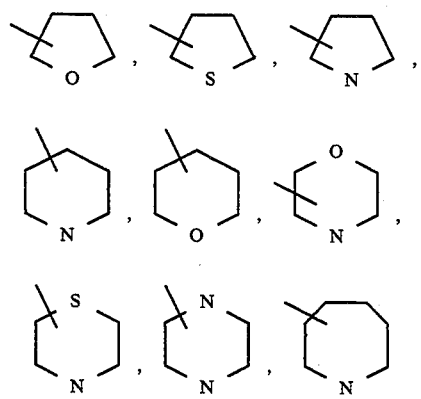

of these, preferred are tetrahydrofuryl, tetrahydrothienyl, pyrrolidyl, piperidyl, tetrahydropyranyl, piperazinyl, morpholinyl and hexahydroazepinyl, and particularly preferred are tetrahydrofuryl, pyrrolidyl, piperidyl, tetrahydropyranyl and morpholinyl.

The heterocyclic residue in the present invention may be condensed with benzene or heterocyclic ring to form those exemplified below.

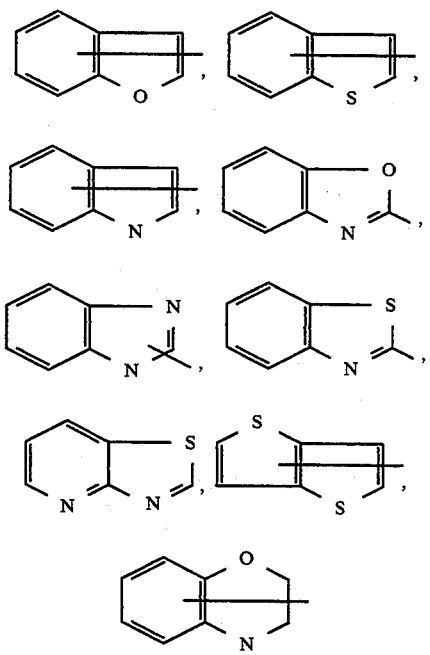

Of these, preferred are those condensed with benzene ring such as benzofuranyl, benzothienyl, indolyl, benzoxazolyl, benzimidazolyl and benzothiazolyl.

The heterocyclic residue described above is unsubstituted or substituted once or twice by halogen such as fluorine, chlorine and bromine, hydroxy, $C_1$-$C_4$ alkyl, $C_1$-$C_4$ alkoxy, $C_1$-$C_4$alkylcarbonyl, $C_1$-$C_4$ alkoxycarbonyl, cyano, primary, secondary or tertiary amine unsubstituted or substituted by $C_1$-$C_4$ alkyl or keto group. The alkyl and alkoxy include those exemplified above for the symbols A and B, and the keto group means those formed by bonding the heterocyclic ring-constituting carbon atom and an oxygen atom through a double bond, such as those exemplified below.

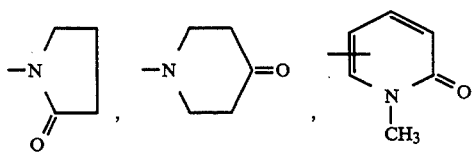

Among the heterocyclic residues described above, preferred are those unsubstituted or substituted by alkyl such as methyl, alkylcarbonyl such as acetyl and propionyl, or methoxy-, ethoxy- or propoxycarbonyl, and particularly preferred are 2-tetrahydrofuryl, pyrrolidyl, piperidyl, tetrahydropyranyl and morpholinyl, which are unsubstituted or substituted by alkyl such as methyl.

The heterocyclic compounds of the formula (I) can be produced in a manner known per se, for example, by reacting the mandelic acid of the formula (II) with the compound of the formula (III), followed by mild oxidation preferably in the presence of an oxidant. The reaction can be readily effected in a solvent at a temperature of about 50° C. to about 150° C. in the presence or absence of an acid catalysts. The oxidant usable includes, for example, chloranil, persulfates, hydrogen peroxide and the like.

The mandelic acid of the formula (II) can be produced in a manner described in, for example, System No. 1106/H410-411, Vol. 10 of Beilsteins Handbuch der Organischen Chemie and enlarged edition thereof. According to the description, 4-hydroxymandelic acid of the following formula (II) a,

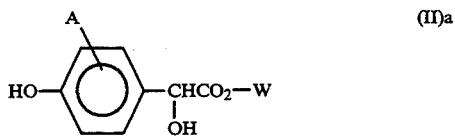
(II)a wherein A is as defined above, and W is a hydrogen atom or a $C_1$-$C_4$ alkyl group, and an alkylating agent of the following formula (II)b,

(II)b wherein $R^1$, X, T, U, l and Q are as defined above, and L is a group capable of being split such as a halogen atom or an arylsulfonyloxy group, can be allowed to react with each other in the presence of an acid binding agent, if necessary, followed by hydrolysis of the ester bonding.

Alternatively, the mandelic acid (II) can be also produced by reacting a bonzaldehyde of the following formula (II)c,

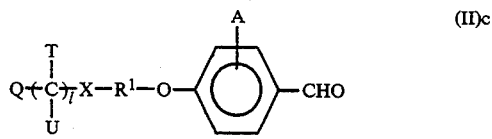
(II)c wherein $R^1$, X, T, U, l, Q and A are as defined above, with sodium hydrogensulfite and sodium cyanide, and then hydrolyzing the resulting mandelonitrile, or by reducing a phenylglyoxylic acid of the following formula (II)d,

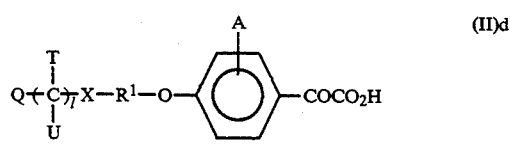
(II)d wherein $R^1$, X, T, U, l, Q and A are as defined above.

The compound of the formula (III) can be produced in a manner described in, for example, Chemische Berichte, Vol. 30, 124 (1897), such that a mandelic acid compound of the following formula (III)a,

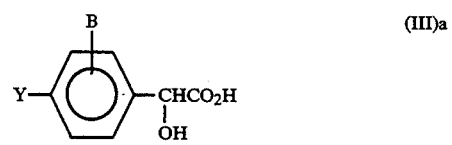
(III)a wherein B and Y are as defined above, and hydroquinone are allowed to react with each other in an acid medium such as 73% sulfuric acid under heating.

The starting compound of the formula (III)a can be produced in a manner similar to that for the production of the compound (II).

The heterocyclic compounds of the formula (I) in accordance with the present invention are useful for dyeing or printing hydrophobic fiber materials, particularly those such as polyester fiber materials. In utilizing the present heterocyclic compound in such field, the compounds (I) can be finely pulverized in an aqueous medium with the aid of naphthalenesulfonic acid/formaldehyde condensate, lignin sulfonic acid or the like, thereby obtaining a liquid dye dispersion. The liquid dye dispersion can be used as it is for the dyeing or printing of fiber materials, or dried with, for example, a spray drier to be made in a powder form.

Dyeing can be carried out by a high temperature dyeing method wherein hydrophobic fiber materials are dipped in an aqueous dye bath and heated to a temperature of 105° C. or higher, preferably 110° to 140° C. under increased pressures, a carrier dyeing method wherein dyeing is carried out in the presence of a carrier such as o-phenylphenol, trichlorobenzene and the like at a relatively high temperature, for example, water-boiling temperature, or a thermosol method wherein the fiber materials are padded with an aqueous dye dispersion and dry-heated at a temperature of 150° to 230° C. for 30 to 60 seconds.

Printing can be carried out by mixing the aqueous dye dispersion with a suitable stock paste to obtain a color paste, printing fiber materials with the color paste and then steaming or thermosol-treating the printed fiber materials.

In addition, the fiber materials can also be dyed by a solvent dyeing method wherein an organic solvent such as trichloroethylene, perchloroethylene and the like is used as a dyeing medium.

The dyed or printed products thus obtained can be subjected, if desired, to after-finish treatments such as softening finish, water-repellenting finish, feel-improving finish, antistatic finish or sanitary finish in a conventional manner.

The present heterocyclic compounds of the formula (I) can be characterized by the facts such that hydrophobic fiber materials, particularly those such as polyester fiber materials, can be dyed or printed in a usual manner using the present compound (I), thereby obtaining dyed or printed products of a brilliant red color excellent in various fastness properties such as light fastness, sublimation fastness and wet fastness and such fastness properties cannot be deteriorated even after heat-set treatment and after-finish treatments. For example, the fiber materials can be dyed using a high concentration of the dye to obtain dyed products of a deep color (e.g. JIS 2/1 depth), and the washing fastness property thereof is robust so that it can be kept at a higher degree even after the heat-set treatments of dyed products than that of those dyed with existing red desperse dyes. Considering the fact that a standard of the washing fastness has been made severer to meet the actual condition of consumers' high demand, the robustness is significant.

The present heterocyclic compounds of the formula (I) can be characterized also by superior dyeability, so that dyed or printed products of a deep color can be readily obtained, with superior build-up property and superior dye bath stability (low pH sensitivity), particularly by the high temperature dyeing method. Moreover, the present compound can be used in combination with other dyes to improve the dye performance and to obtain a variety of color.

In consideration of the characteristic features described above, the heterocyclic compounds of the present invention can be advantageously used particularly for the dyeing of apparels such as sportswear, which are required to be dyed usually in a deep color and have superior washing fastness because they are to be washed again and again.

The present invention is illustrated in more detail with reference to the following Examples, which are only illustrative but not limitative for the scope of the present invention.

EXAMPLE 1

A mixture of 4-tetrahydrofurfuryloxymandelic acid (2.65 parts) and 5-hydroxy-2-oxo-3-phenyl-2,3-dihydrobenzofuran ( 2.26 parts ) was kept at 80° C. for 6 hours in a mixed solvent of acetic acid (38 parts) and sulfuric acid (2 parts), and thereafter, ammonium persulfate (2.34 parts) was added to the reaction mixture. The resulting mixture was kept at 100° C. for additional 1 hour, thereafter cooled to ambient temperature, and then mixed with methanol (50 parts).

The crystals produced were collected on a filter, washed with water and dried to obtain a compound of the following formula (1).

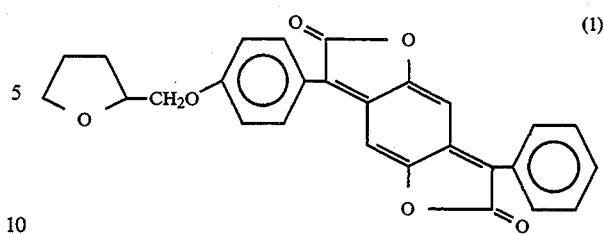

The maximum absorption wave length ($\lambda$ max) of the compound in dimethylformamide was found to be 503 nm.

EXAMPLE 2

The compound of the formula (1) obtained in Example 1 (1.0 part) was finely pulverized in an aqueous medium with the aid of naphthalenesulfonic acid-formaldehyde condensate (3.0 parts) . The resulting dye dispersion was dried to form powder.

Polyester cloth (10 parts, Tetron jersey, a product of Teijin Limited, in Japan) was dipped in a dyebath containing the powder (0.6 part), and dyeing was continued for 60 minutes at 130° to 135° C. under increased pressures. The dyed cloth was subjected to reduction-rinsing treatment at 85° C. for 10 minutes in a solution of sodium hydroxide (3 parts), hydrosulfite (3 parts) and a betaine amphoteric surfactant (3 parts) in water (3000 parts), washed with water and then dried, thereby obtaining a dyed product of a brilliant red color superior in light fastness, sublimation fastness and wet fastness.

The dyed product was dipped in a padding liquor containing a soft-finishing agent (10 g/l, Sumitex Softener LK-1, a product of Sumitomo Chemical Co., Ltd., in Japan) and an anti-static agent (5 g/l, Sumistat F-1, a product of Sumitomo Chemical Co., Ltd., in Japan), squeezed uniformly at a pick-up of 80%, again dipped into the same padding liquor as above, squeezed at the same level as above, pre-dried at 80° C. for 2 minutes and then subjected to heat set at 170° C. for 1 minute. The thus after-finished dyed product was found to have a superior washing fastness.

EXAMPLE 3

The compound of the formula (1) obtained in Example 1 (1.3 parts) was finely pulverized with the aid of lignin sulfonic acid (3.7 parts). To the resulting dispersion were added hot water (35 parts) and a half emulsion paste (60 parts) having the following composition.

| O/W Emulsion | 300 parts |
| --- | --- |
| Stock paste (12% Maypro gum) | 694 parts |
| Sodium chlorate | 4 parts |
| Tartaric acid | 2 parts |

Polyester cloth (Tetron tropical, a product of Teijin Limited in Japan) was printed with the above obtained printing paste, pre-dried and steamed for 7 minutes at 170° C. under atmospheric pressure. The printed cloth was subjected to reduction rinsing treatment, washing with water and softening and anti-static finishings in this order in a manner similar to that of Example 2. The thus obtained printed product of a red color was found to have superior light, sublimation and wet fastness properties, particularly washing fastness.

EXAMPLE 4

Example 1 was repeated, provided that 4-(tetrahydropyran-2-ylmethoxy)madelic acid was used in place of 4-tetrahydrofurfuryl-oxy-mandelic acid, thereby obtaining a compound of the following formula (2) ($\lambda_{max}^{DMF}$503 nm).

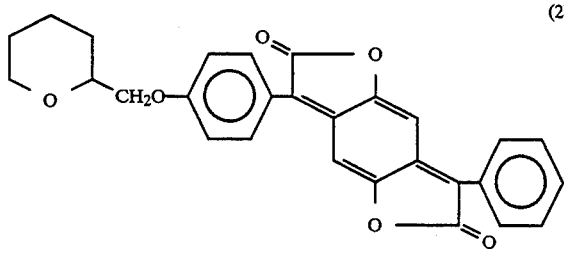

(2)

Using the compound, Example 2 was repeated to obtain a dyed product superior in light, sublimation and wet fastness properties, particularly superior in washing fastness.

EXAMPLES 5 to 72

In a manner similar to that of Example 1, respective compounds as shown in the following table 1 were obtained. These compounds can be used for dyeing polyester cloth to obtain dyed product having superior washing fastness.

TABLE 1

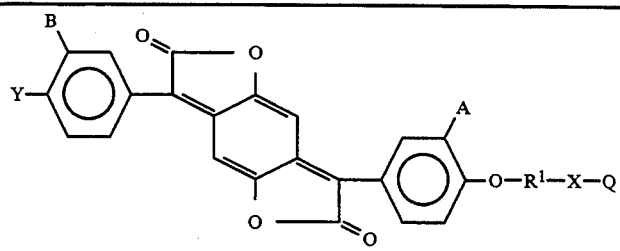

| Example No. | A | B | Y | $R^1$ | X | Q |
|---|---|---|---|---|---|---|
| 5 | H | H | H | —CH₂CH₂— | direct linkage | tetrahydrofuran-2-yl |
| 6 | H | H | H | —CH₂CH₂CH₂— | direct linkage | tetrahydrofuran-2-yl |
| 7 | H | H | H | —CH₂— | direct linkage | 5-methyltetrahydrofuran-2-yl |
| 8 | H | H | H | —(CH₂)₃CH(CH₃)CH₂— | direct linkage | morpholin-4-yl |
| 9 | H | H | H | —CH₂— | direct linkage | 2,5-dimethyltetrahydrofuran-2-yl |
| 10 | H | H | H | —CH₂CH₂— | direct linkage | tetrahydrothiophen-2-yl |
| 11 | H | H | H | —CH₂CH₂— | direct linkage | pyrrolidin-1-yl |
| 12 | H | H | H | —CH₂CH₂— | direct linkage | piperidin-1-yl |

TABLE 1-continued

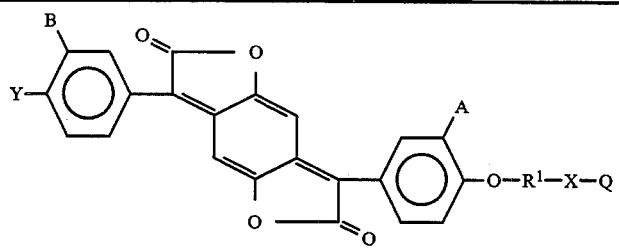

| Example No. | A | B | Y | R¹ | X | Q |
|---|---|---|---|---|---|---|
| 13 | H | H | H | —CH$_2$— | direct linkage | 3-methylmorpholine |
| 14 | H | H | H | —(CH$_2$)$_4$— | direct linkage | 4-oxopiperidine |
| 15 | H | H | H | —CH$_2$CH$_2$— | direct linkage | 3,5-dimethyltetrahydrofuran |
| 16 | H | H | H | —CH$_2$— | direct linkage | 1-ethyl-2-methylpyrrolidine |
| 17 | H | H | H | —CH$_2$CH(OH)CH$_2$— | direct linkage | piperidine |
| 18 | H | H | H | —CH$_2$CH$_2$CH$_2$— | —C(=O)— | piperidine |
| 19 | H | H | H | —(CH$_2$)$_4$— | direct linkage | 2,5-dimethylpyrrolidine |
| 20 | H | H | H | —CH$_2$— | direct linkage | 1,3-dimethylpiperidine |
| 21 | H | H | H | —CH$_2$CH$_2$— | direct linkage | caprolactam (hexahydro-2-oxoazepine) |

TABLE 1-continued
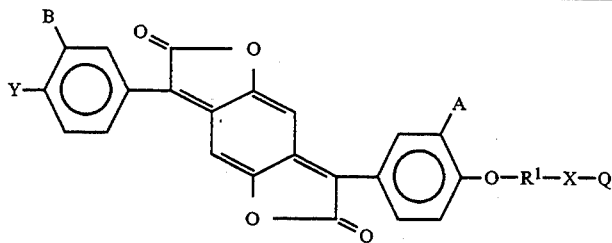
| Example No. | A | B | Y | R¹ | X | Q |
|---|---|---|---|---|---|---|
| 22 | H | H | H | —CH₂CH₂CH₂— | direct linkage | 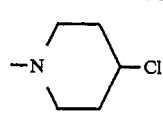 |
| 23 | H | H | H | —CH₂CH₂— | direct linkage | 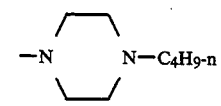 |
| 24 | H | H | H | —CH₂— | direct linkage | 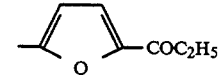 |
| 25 | H | H | H | —CH₂CH₂— | direct linkage | 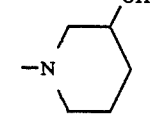 |
| 26 | H | H | H | —CH₂CH₂— | direct linkage | 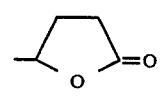 |
| 27 | CH₃O— | H | H | —CH₂— | direct linkage | 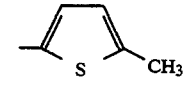 |
| 28 | H | (CH₃)₂CHCH₂O— | H | —CH₂— | direct linkage | 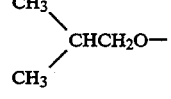 |
| 29 | H | —OCH₂O— | | —CH₂— | direct linkage | 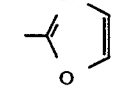 |
| 30 | H | CH₃ | H | —CH₂CH₂— | —NH— | 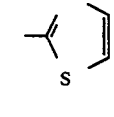 |
| 31 | H | H | CH₃ | —CH₂CH₂— | —O— | 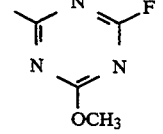 |

TABLE 1-continued

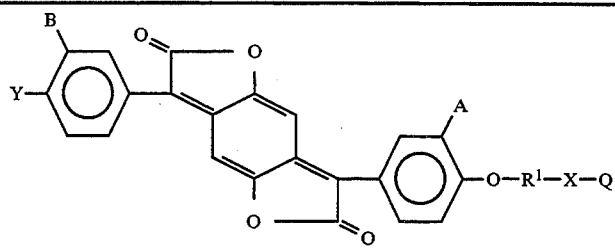

| Example No. | A | B | Y | R¹ | X | Q |
|---|---|---|---|---|---|---|
| 32 | H | H | n-C₃H₇O— | —CH₂CH₂— | direct linkage | 3-methyl-5-oxo-4,5-dihydro-1H-pyrazol-1-yl |
| 33 | H | H | —OC₂H₄—N(imidazolyl) | —CH₂CH₂— | direct linkage | 1-imidazolyl |
| 34 | H | H | H | —CH₂CH₂— | —S— | 6-chloro-2-benzothiazolyl |
| 35 | H | H | H | —CH₂CH₂— | —O— | 2-benzimidazolyl (NH) |
| 36 | H | H | H | —CH₂CH₂— | —O— | 1-methyl-5-methylindol-2-yl |
| 37 | H | H | H | —CH₂CH₂— | —N(CH₃)— | 2-benzothienyl |
| 38 | H | H | H | —CH₂CH₂— | —S— | 2-benzoxazolyl |
| 39 | H | H | H | —CH₂CH₂— | —S(=O)— | 2-benzoxazolyl |
| 40 | H | H | H | —CH₂CH₂CH₂— | —S(=O)₂— | 2-benzoxazolyl |
| 41 | H | H | H | —CH₂CH₂CH₂— | —O—C(=O)— | 1,5-dimethylpyrrol-2-yl |

TABLE 1-continued

Structure: Y-(3-B-phenyl)-C(=C...quinone-dioxole system...)=C-(3-A-phenyl)-O-R¹-X-Q

| Example No. | A | B | Y | R¹ | X | Q |
|---|---|---|---|---|---|---|
| 42 | H | H | H | —CH₂CH₂— | —C(=O)—NH— | 5-(n-C₃H₇O₂C)-thiophen-2-yl |
| 43 | H | H | H | —CH₂CH₂— | —O—C(=O)— | 5-Br-thiophen-2-yl |
| 44 | H | H | H | —CH₂— | —C(=O)—N(CH₃)— | 5-cyano-6-(n-C₄H₉NH)-2-methylpyridin-3-yl |
| 45 | H | H | H | —CH₂CH₂CH₂— | direct linkage | 6-methyl-tetrahydropyran-2-yl |
| 46 | H | H | H | —CH₂CH₂CH₂— | direct linkage | 6-methylpyridin-2-yl |
| 47 | H | H | H | —CH₂CH₂— | direct linkage | 2-oxopiperidin-1-yl |
| 48 | H | H | H | —CH₂CH₂— | direct linkage | 6-methyl-tetrahydropyran-2-yl |
| 49 | H | H | H | —CH₂CH₂CH₂— | direct linkage | morpholin-4-yl |
| 50 | H | H | H | —CH₂CH₂CH₂— | direct linkage | piperidin-1-yl |
| 51 | H | H | H | —CH₂CH₂— | direct linkage | morpholin-4-yl |
| 52 | H | H | H | —CH₂CH₂CH₂— | direct linkage | 5-methyl-tetrahydrofuran-2-on-5-yl |

TABLE 1-continued

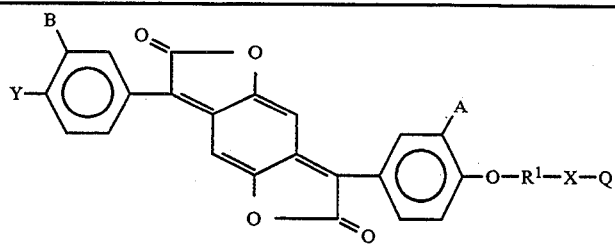

| Example No. | A | B | Y | R¹ | X | Q |
|---|---|---|---|---|---|---|
| 53 | H | H | H | —CH₂CHCH₂—<br>        \|<br>        OH | direct linkage | azepan-1-yl |
| 54 | H | H | H | —CH₂CH₂— | direct linkage | 1-methylpyrrolidin-2-yl |
| 55 | H | H | H | —CH₂CH₂CH₂— | direct linkage | tetrahydrofuran-3-yl |
| 56 | H | H | H | —CH₂CH₂CH₂— | direct linkage | 5H-furan-2-one-5-yl |
| 57 | H | H | H | —CH₂CH₂— | direct linkage | tetrahydrothiophen-3-yl |
| 58 | H | H | H | —CH₂CH₂— | direct linkage | 1-methylpiperidin-2-yl |
| 59 | H | H | H | —CH₂CH₂— | direct linkage | 2-oxopiperidin-1-yl |
| 60 | H | H | H | —CH₂CH₂— | direct linkage | tetrahydrofuran-3-yl |
| 61 | H | H | H | —CH₂— | direct linkage | tetrahydrofuran-3-yl |
| 62 | H | H | H | —CH₂CH₂— | direct linkage | 1-acetyl-2-methylpiperidin-2-yl |

TABLE 1-continued
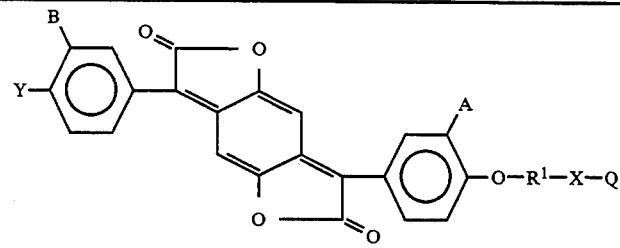
| Example No. | A | B | Y | R¹ | X | Q |
|---|---|---|---|---|---|---|
| 63 | H | H | H | —CH$_2$CH$_2$— | direct linkage | 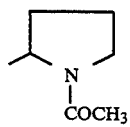 |
| 64 | H | H | H | —CH$_2$— | direct linkage | 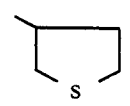 |
| 65 | H | H | H | —CH$_2$CH$_2$— | direct linkage | 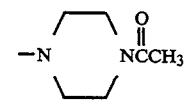 |
| 66 | H | H | H | —CH$_2$— | direct linkage | 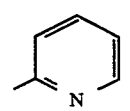 |
| 67 | H | H | H | —CH$_2$— | direct linkage | 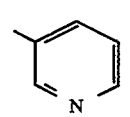 |
| 68 | H | H | H | —CH$_2$CH$_2$— | direct linkage | 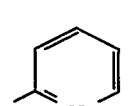 |
| 69 | H | H | H | —CH$_2$CH$_2$— | direct linkage | 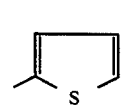 |
| 70 | H | H | H | —CH$_2$CH$_2$— | direct linkage | 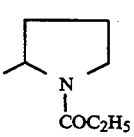 |
| 71 | H | H | H | —CH$_2$CH$_2$— | direct linkage | 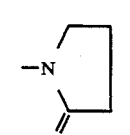 |
| 72 | H | H | H | —CH$_2$CH$_2$— | direct linkage | 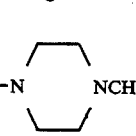 |

EXAMPLE 73

Example 1 was repeated, provided that 4-(2-tetrahydrofuryloxyethoxy) mandelic acid was used in place of the 4-tetrahydrofurfuryloxymandelic acid, thereby obtaining a compound of the following formula (3) ($\lambda_{max}^{DMF}$504 nm).

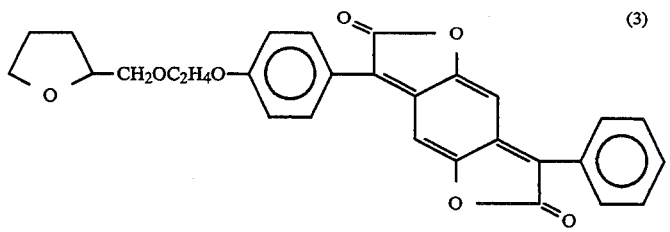

(3)

Using the compound, Example 2 was repeated to obtain a dyed product superior in light, sublimation and wet fastness properties, particularly superior in washing fastness.

EXAMPLES 74 to 132

In a manner similar to that of Example 1, respective compounds as shown in the following table 2 were obtained. These compounds can be used for dyeing polyester cloth to obtain dyed products having superior washing fastness.

TABLE 2

| Example No. | A | B | Y | $R^1$ | X | l | T | U | Q |
|---|---|---|---|---|---|---|---|---|---|
| 74 | H | H | H | —(CH$_2$)$_4$— | —O— | 1 | —C$_2$H$_5$ | H | CH$_3$-substituted tetrahydrofuranyl-CH$_3$ |
| 75 | H | H | H | —CH$_2$CH(OH)CH$_2$— | —O— | 2 | H | H | tetrahydrofuranyl-CH$_3$ |
| 76 | H | H | H | —CH$_2$CH(OCH$_3$)CH$_2$— | —O— | 2 | H | H | tetrahydrofuranyl-CH$_3$ |
| 77 | H | H | H | —CH$_2$CH(OCOC$_3$H$_7$-n)CH$_2$— | —O— | 2 | H | H | tetrahydrofuranyl-CH$_3$ |
| 78 | H | CH$_3$O | CH$_3$O | —CH$_2$CH$_2$— | —S— | 3 | H | H | furyl |
| 79 | H | H | CH$_3$ | —CH$_2$CH$_2$CH$_2$— (with CH$_3$ branch) | —O— | 1 | —CH$_3$ | CH$_3$ | furyl |
| 80 | H | H | H | —CH$_2$— | —C(=O)—NH— | 1 | H | H | tetrahydrofuranyl |
| 81 | H | H | H | —CH$_2$CH$_2$— | —OC(=O)— | 2 | H | H | morpholino (—N(CH$_2$CH$_2$)$_2$O) |

TABLE 2-continued
| Example No. | A | B | Y | R¹ | X | l | T | U | Q |
|---|---|---|---|---|---|---|---|---|---|
| 82 | CH₃O | H | H | —CH₂— | —C(=O)—O— | 2 | H | H |  |
| 83 | H | H | H | —CH₂CH₂CH₂— | —NH—C(=O)— | 1 | H | H |  |
| 84 | H | H | H | —CH₂CH₂— | —O— | 2 | H | H |  |
| 85 | H | H | H | —CH₂CH₂— | —O— | 3 | H | H |  |
| 86 | H | H | CH₃ | —CH₂— | —C(=O)—O— | 2 | H | H |  |
| 87 | H | H | H | —CH₂CH(OH)CH₂— | —O— | 1 | H | H |  |
| 88 | H | H | H | —CH₂CH₂CH₂— | —O— | 2 | H | H |  |
| 89 | H | H | H | —(CH₂)₆— | —O— | 1 | H | H |  |
| 90 | H | H | H | —CH₂CH(OCH₃)CH₂— | —O— | 2 | H | H |  |
| 91 | H | H | H | —(CH₂)₆— | —O— | 1 | H | H |  |
| 92 | H | H | H | —CH₂CH₂CH₂— | —O— | 2 | H | H |  |

TABLE 2-continued
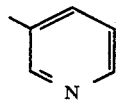
| Example No. | A | B | Y | R¹ | X | l | T | U | Q |
|---|---|---|---|---|---|---|---|---|---|
| 93 | H | H | H | —CH₂CH₂CH₂— | —O— | 1 | H | H | 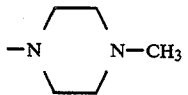 |
| 94 | H | H | H | —CH₂CH₂CH₂— | —O— | 2 | H | H | 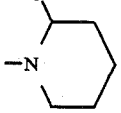 |
| 95 | H | H | H | —CH₂CH₂CH₂— | —O— | 2 | H | H | 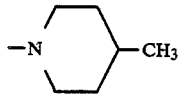 |
| 96 | H | H | H | —CH₂CH₂CH₂— | —O— | 2 | H | H | 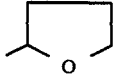 |
| 97 | H | H | H | —CH₂CH₂CH₂— | —O— | 1 | H | H | 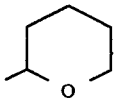 |
| 98 | H | H | H | —CH₂CH₂CH₂— | —O— | 1 | H | H | 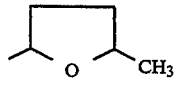 |
| 99 | H | H | H | —CH₂CH₂CH₂— | —O— | 1 | H | H | 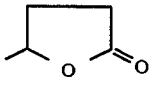 |
| 100 | H | H | H | —CH₂CH₂CH₂— | —O— | 1 | H | H | 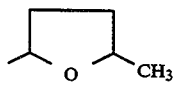 |
| 101 | H | H | H | —CH₂CHCH₂—<br>         OH | —O— | 1 | H | H | 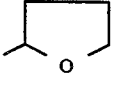 |
| 102 | H | H | H | —CH₂CH₂CH₂— | —O— | 2 | H | H |  |
| 103 | H | H | CH₃ | —CH₂— | —OCO— | 2 | H | H | 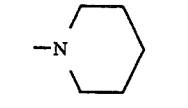 |

TABLE 2-continued

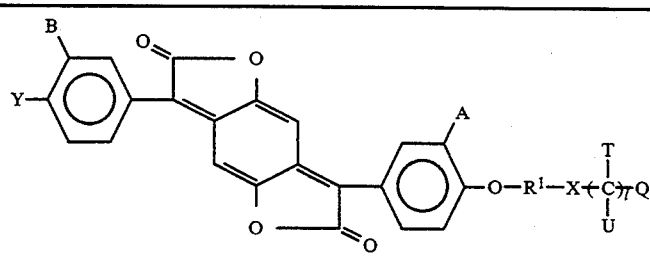

| Example No. | A | B | Y | R¹ | X | l | T | U | Q |
|---|---|---|---|---|---|---|---|---|---|
| 104 | H | H | H | —CH₂CH₂— | —O— | 2 | H | H | piperidin-1-yl |
| 105 | H | H | H | —CH₂CH₂CH₂— | —O— | 2 | H | H | 2-oxopyrrolidin-1-yl |
| 106 | H | H | H | —CH₂CH₂CH₂— | —O— | 2 | H | H | piperidin-1-yl |
| 107 | H | H | H | —CH₂CH₂CH₂— | —O— | 2 | H | H | morpholin-4-yl |
| 108 | H | H | H | —CH₂CH₂— | —O— | 2 | H | H | azepan-1-yl |
| 109 | H | H | H | —CH₂CH₂— | —O— | 2 | H | H | 2-oxopiperidin-1-yl |
| 110 | H | H | H | —CH₂CH₂— | —O— | 1 | H | H | 5-methylfuran-2-yl |
| 111 | H | H | H | —CH₂CH₂CH₂— | —O— | 1 | H | H | 5-methyl-2-oxo-2,5-dihydrofuran-2-yl |
| 112 | H | H | H | —CH₂CH₂— | —O— | 2 | H | H | 1,2-dimethylpiperidin-2-yl |
| 113 | H | H | H | —CH₂CH₂— | —O— | 2 | H | H | tetrahydrothiophen-3-yl |

TABLE 2-continued
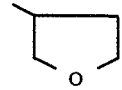
| Example No. | A | B | Y | R¹ | X | l | T | U | Q |
|---|---|---|---|---|---|---|---|---|---|
| 114 | H | H | H | —CH₂CH₂CH₂— | —O— | 1 | H | H | 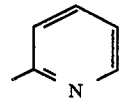 |
| 115 | H | H | H | —CH₃CH₃CH₃— | —O— | 1 | H | H | 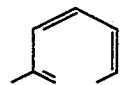 |
| 116 | H | H | H | —CH₂CH₂— | —O— | 3 | H | H | 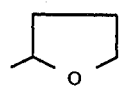 |
| 117 | H | H | H | —CH₂CH₂— | —O— | 2 | H | H | 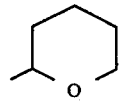 |
| 118 | H | H | H | —CH₂CH₂— | —O— | 1 | H | H | 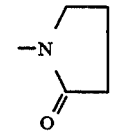 |
| 119 | H | H | H | —CH₂CH₂— | —O— | 2 | H | H | 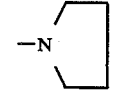 |
| 120 | H | H | H | —CH₂CH₂— | —O— | 2 | H | H | 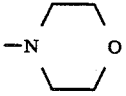 |
| 121 | H | H | H | —CH₂CH₂— | —O— | 2 | H | H | 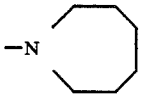 |
| 122 | H | H | H | —CH₂CH₂— | —O— | 2 | H | H | 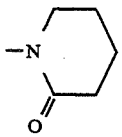 |
| 123 | H | H | H | —CH₂CH₂— | —O— | 2 | H | H |  |
| 124 | H | H | H | —CH₂— | $-\overset{\overset{O}{\|}}{C}O-$ | 1 | H | H | 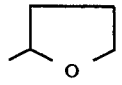 |

TABLE 2-continued

| Example No. | A | B | Y | R¹ | X | l | T | U | Q |
|---|---|---|---|---|---|---|---|---|---|
| 125 | H | H | H | —CH₂— | —CO— (O) | 1 | H | H | 2,5-dimethyltetrahydrofuran-yl |
| 126 | H | H | H | —CH₂— | —CO— (O) | 2 | H | H | pyrrolidin-1-yl |
| 127 | H | H | H | —CH₂CH₂— | —CO— (O) | 1 | H | H | tetrahydrofuran-2-yl |
| 128 | H | H | H | —CH₂— | —CO— (O) | 2 | H | H | piperidin-1-yl |
| 129 | H | H | H | —CH₂— | —CO— (O) | 2 | H | H | 2-oxopyrrolidin-1-yl |
| 130 | H | H | H | —CH₂—CH₂— | —CO— (O) | 1 | H | H | 2,5-dimethyltetrahydrofuran-yl |
| 131 | H | H | H | —CH₂— | —CO— (O) | 1 | H | H | tetrahydropyran-2-yl |
| 132 | H | H | H | —CH₂— | —CO— (O) | 2 | H | H | hexahydro-2-oxoazepin-1-yl |

EXAMPLES 133 to 140

In a manner similar to that of Example 1, respective compounds as shown in the following table 3 were obtained. These compounds can be used for dyeing polyester cloth to obtain dyed products having superior washing fastness.

TABLE 3

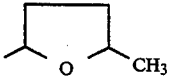

| Example No. | A | B | Y | R¹ | X | Q |

| | | | | | |
|---|---|---|---|---|---|
| 133 | 3-Br | H | H | —CH$_2$— | direct linkage 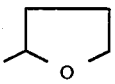 |
| 134 | H | 3-Br | H | —CH$_2$— | direct linkage 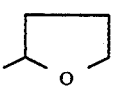 |
| 135 | H | H | Br | —CH$_2$— | direct linkage 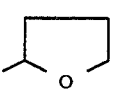 |
| 136 | 3-Cl | H | H | —CH$_2$— | direct linkage 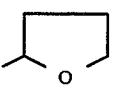 |
| 137 | H | 3-Cl | H | —CH$_2$— | direct linkage 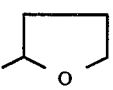 |
| 138 | H | H | Cl | —CH$_2$— | direct linkage 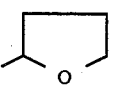 |
| 139 | H | 2-Cl | H | —CH$_2$— | direct linkage 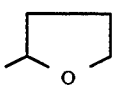 |
| 140 | H | 2-Br | H | —CH$_2$— | direct linkage 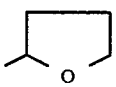 |

We claim:

1. A heterocyclic compound of the formula

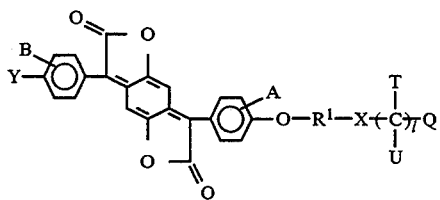

wherein:

A and B are each independently selected from the group consisting of hydrogen, halogen, C$_1$ to C$_4$ alkyl and C$_1$ to C$_4$ alkoxy;

R$^1$ is selected from the group consisting of methylene, straight or branched C$_2$ to C$_6$ alkylene, and straight or branched C$_2$ to C$_6$ alkylene which is substituted by hydroxy group, C$_1$ to C$_4$ alkoxy or C$_1$ to C$_4$ alkylcarbonyloxy;

X is selected from the group consisting of direct linkage,

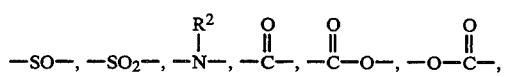

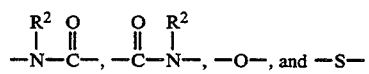

in which R$^2$ is selected from the group consisting of hydrogen and C$_1$ to C$_4$ alkyl;

T is selected from the group consisting of hydrogen and C$_1$ to C$_4$ alkyl;

U is selected from the group consisting of hydrogen and C$_1$ to C$_4$ alkyl;

l is 0 or an integer of 1 to 3;

Q is a heterocyclic residue selected from the group consisting of furyl, thienyl, pyrrolyl, pyridyl, pyranyl, thiazolyl, oxazolyl, pyrazolyl, imidazolyl, thiadiazolyl, s-triazinyl, benzofuranyl, benzothienyl, indolyl, benzoxazolyl, benzimidazolyl, benzothiazolyl, thiazolo[4,5-b]pyridinyl, thieno[3,2-b]thienyl, 2,3-dihydro-4H-1,4-benzoxazinyl, tetrahydrofuryl, tetrahydrothienyl, pyrrolidyl, piperidyl, tetrahydropyranyl, piperazinyl, morpholinyl, thiazanyl and hexahydroazepinyl, said heterocyclic residue Q being unsubstituted or substituted once or twice by halogen, hydroxy, C$_1$ to C$_4$ alkyl, C$_1$ to C$_4$ alkoxy, C$_1$ to C$_4$ alkylcarbonyl, C$_1$ to C$_4$ alkoxycarbonyl, cyano, keto, or primary, secondary, or tertiary amino which is unsubstituted or substituted by C$_1$ to C$_4$ alkyl; and Y is selected from the group consisting of hydrogen, halogen, C$_1$ to C$_4$ alkoxy, C$_1$ to C$_4$ alkyl, and a group of the formula

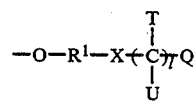

in which R$^1$, X, T, U, Q and l are as defined above; provided that Y an B can be taken together with each other to form a methylenedioxy group.

2. A heterocyclic compound according to claim 1, wherein Y is selected from the group consisting of hydrogen, halogen, C$_1$ to C$_4$ alkoxy, and C$_1$ to C$_4$ alkyl.

3. A heterocyclic compound of the formula,

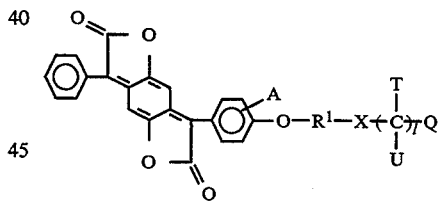

wherein

R$^1$ is selected from methylene, straight or branched chain C$_1$-C$_6$ alkylene which is unsubstituted or substituted by a hydroxy group, C$_1$-C$_4$ alkoxy and C$_1$-C$_4$ alkycarbonyloxy;

X is selected from direct linkage,

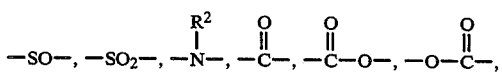

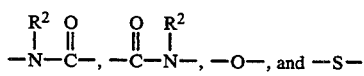

wherein R$^2$ is selected from hydrogen and C$_1$-C$_4$ alkyl;

T and U are each independently selected from hydrogen and C$_1$-C$_4$ alkyl;

l is 0 or an integer of 1 to 3; and

Q is selected from the group consisting of furyl, thienyl, pyrrolyl, pyridyl, pyranyl, thiazolyl, oxazolyl, pyrazolyl, imidazolyl, thiadiazolyl, s-triazinyl, benzofuranyl, benzothienyl, indolyl, benzoxazolyl, benzimidazolyl, benzothiazolyl, thiazolo[4,5-b]pyridinyl, thieno[3,2-b]thienyl, 2,3-dihydro-4H-1,4-benzoxazinyl, tetrahydrofuryl, tetrahydrothienyl, pyrrolidyl, piperidyl, tetrahydropyranyl, piperazinyl, morpholinyl, thiazanyl and hexahydroazepinyl.

4. The compound according to claim 3, wherein Q is unsubstituted or substituted once or twice by halogen, hydroxy, $C_1$-$C_4$ alkyl, $C_1$-$C_4$ alkoxy, $C_1$-$C_4$ alkoxycarbonyl, cyano, keto, or primary, secondary or tertiary amino which is unsubstituted or substituted by $C_1$-$C_4$ alkyl.

5. The compound according to claim 3, wherein Q is furyl, thienyl, pyrrolyl, pyridyl, pyranyl, thiazolyl, oxazolyl, pyrazolyl, imidazolyl, thiadiazolyl, s-triazinyl, benzofuranyl, benzothienyl, indolyl, benzoxazolyl, benzimidazolyl or benzothiazolyl.

6. The compound according to claim 3, wherein Q is tetrahydrofuryl, tetrahydrothienyl, pyrrolidyl, piperidyl, tetrahydropyranyl, piperazinyl, morpholinyl or hexahydrozepinyl.

7. The compound according to claim 3, wherein Q is 2-tetrahydrofuryl, tetrahydropyranyl, piperidyl, pyrrolidyl or morpholinyl unsubstituted or substituted by $C_1$-$C_4$ alkyl.

8. The compound according to claim 3, wherein l is 0.

9. The compound according to claim 3, wherein $R^1$ is methylene or straight $C_2$-$C_4$ alkylene.

10. A compound of the formula

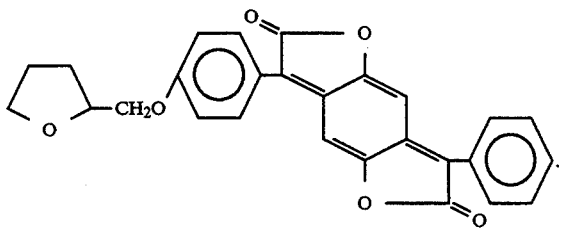

11. A disperse dye composition comprising a heterocyclic compound according to claim 1.

12. A pulverulent disperse dye composition comprising at least one heterocyclic compound of the formula,

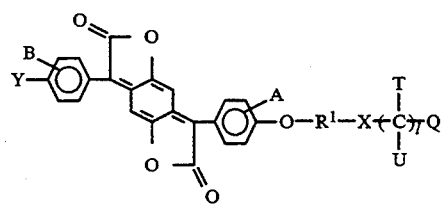

wherein:

A and B are each independently selected from the group consisting of hydrogen, halogen, $C_1$ to $C_4$ alkyl and $C_1$ to $C_4$ alkoxy;

$R^1$ is selected from the group consisting of methylene, straight or branched $C_2$ to $C_6$ alkylene, and straight or branched $C_2$ to $C_6$ alkylene which is substituted by hydroxy group, $C_1$ to $C_4$ alkoxy or $C_1$ to $C_4$ alkylcarbonyloxy;

X is selected from the group consisting of direct linkage,

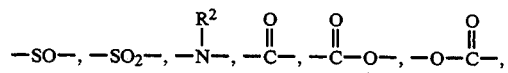

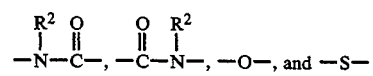

in which $R^2$ is selected from the group consisting of hydrogen and $C_1$ to $C_4$ alkyl;

T is selected from the group consisting of hydrogen and $C_1$ to $C_4$ alkyl;

U is selected from the group consisting of hydrogen and $C_1$ to $C_4$ alkyl;

l is 0 or an integer of 1 to 3;

Q is a heterocyclic residue selected from the group consisting of furyl, thienyl, pyrrolyl, pyridyl, pyranyl, thiazolyl, oxazolyl, pyrazolyl, imidazolyl, thiadiazolyl, s-triazinyl benzofuranyl, benzothienyl, indolyl, benzoxazolyl, benzimidazolyl, benzothiazolyl, thiazolo[4,5-b]pyridinyl, thieno[3,2-b]thienyl, 2,3-dihydro-4H-1,4-benzoxazinyl, tetrahydrofuryl, tetrahydrothienyl, pyrrolidyl, piperidyl, tetrahydropyranyl, piperazinyl, morpholinyl, thiazanyl and hexahydroazepinyl, said heterocyclic residue Q being unsubstituted or substituted once or twice by halogen, hydroxy, $C_1$ to $C_4$ alkyl, $C_1$ to $C_4$ alkoxy, $C_1$ to $C_4$ alkylcarbonyl, $C_1$ to $C_4$alkoxycarbonyl, cyano, keto, or primary, secondary, or tertiary amino which is unsubstituted or substituted by $C_1$ to $C_4$ alkyl; and Y is selected from the group consisting of hydrogen, halogen, $C_1$ to $C_4$ alkoxy, $C_1$ to $C_4$ alkyl, and a group of the formula

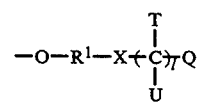

in which $R^1$, X, T, U, Q and l are as defined above; provided that Y and B can be taken together with each other to form a methylenedioxy group.

13. A process for printing or dyeing a hydrophobic fiber material, which comprises contacting the fiber material with a heterocyclic compound according to claim 1.

14. A hydrophobic fiber material dyed or printed by the process according to claim 13.

* * * * *